United States Patent
Wu et al.

(10) Patent No.: US 8,654,337 B2
(45) Date of Patent: Feb. 18, 2014

(54) TURBIDITY SENSOR

(75) Inventors: Shang-Jung Wu, Taoyuan (TW); Zen-Chyuan Chen, Taoyuan (TW)

(73) Assignee: Solteam Opto, Inc., Taoyuan (TW)

( * ) Notice: Subject to any disclaimer, the term of this patent is extended or adjusted under 35 U.S.C. 154(b) by 135 days.

(21) Appl. No.: 13/067,981

(22) Filed: Jul. 13, 2011

(65) Prior Publication Data

US 2013/0016354 A1  Jan. 17, 2013

(51) Int. Cl.
*G01N 21/00* (2006.01)
*G01N 21/25* (2006.01)
*G01J 1/00* (2006.01)
*G01J 1/46* (2006.01)
*G01J 1/42* (2006.01)
*G01J 1/40* (2006.01)
*G01B 9/021* (2006.01)

(52) U.S. Cl.
USPC ........... 356/441; 356/213; 356/234; 356/413; 356/218; 356/215; 356/457

(58) Field of Classification Search
USPC .......... 356/339, 213, 234, 413, 441, 215, 218
See application file for complete search history.

(56) References Cited

U.S. PATENT DOCUMENTS

| 5,486,816 A | * | 1/1996 | Ariga et al. | 340/630 |
| 2002/0159062 A1 | * | 10/2002 | Ottens et al. | 356/339 |
| 2012/0002206 A1 | * | 1/2012 | Giordano et al. | 356/441 |

FOREIGN PATENT DOCUMENTS

WO  WO2010102166  * 10/2010

* cited by examiner

*Primary Examiner* — Tarifur Chowdhury
*Assistant Examiner* — Sunghee Y Gray
(74) *Attorney, Agent, or Firm* — Bacon & Thomas, PLLC

(57) ABSTRACT

A turbidity sensor for sensing the turbidity of a fluid in a working chamber in a household appliance is disclosed to include a light-transmissive body shell defining therein an accommodation chamber and covered with a cover member, and a sensor module, which includes a circuit board mounted in the accommodation chamber inside the body shell, a holder block a set of light-transmitting devices and a set of light-receiving devices on the circuit board in a right angle relationship for emitting light onto the fluid and picking up reflected light from suspended particles/impurities in the fluid for determination of the turbidity of the fluid.

10 Claims, 12 Drawing Sheets

TURBIDITY SENSOR

BACKGROUND OF THE INVENTION

1. Field of the Invention

The present invention relates to turbidity sensing technology and more particularly, to a turbidity sensor for installation in a household appliance for sensing the turbidity of a fluid in a working chamber in the household appliance during operation of the household appliance without interfering flowing of the fluid in the working chamber.

2. Description of the Related Art

Following fast development of electronic technology, many advanced electrical and electronic household appliances are created to service people, bringing convenience to people, helping people save much labor and time and improving the quality and comfort of people's daily living. Many household appliances, such as washing machines and dishwashers, must be connected to a water source and use with a detergent or cleaning agent during working. During the operation of a household appliance to wash thins, such as clothes or dishes, the turbidity of the working fluid will be increased due to the effect of applied detergent, suspended particles and/or any other impurities. Therefore, clean water must be supplied to the working chamber of the household appliance several times before the turbidity of the washing water (working fluid) in the working chamber drops to a predetermined level. Therefore, regular household cleaning appliances (washing machine, dishwasher) are commonly equipped with a turbidity sensor using light-emitting means and light-receiving means for detecting the turbidity of the washing water (working fluid). Subject to the detection of the turbidity sensor, the household appliance can determine the operating mode. Conventional household appliances have different designs and provide different control modes. During the operation of a household appliance, the machine must be interrupted so that the turbidity sensor can detect the turbidity of the working fluid. After turbidity detection, the machine resumes the washing operation. This sensing method wastes much time.

Referring to FIGS. 10~12, the prior art discloses a turbidity sensor design entitled "Turbidity sensor with temperature sensing for household appliances" for household appliances, in particular washing machines and dishwashers. According to this design, the turbidity sensor comprises a housing A having first and second housing fingers A1;A2, a first optical element A3 arranged in the first housing finger A1, a second optical element A4 arranged in the second housing finger A2 and a temperature sensor A5 arranged in the second housing finger A2. The first optical element A3 and the second optical element A4 are adapted for sensing of the turbidity of a cleaning medium at least partially surrounding the housing A. The temperature sensor A is adapted for sensing the temperature of the cleaning medium.

In application, the aforesaid prior art design still has drawbacks as follows:

(1) The first optical element A3 and the second optical element A4 are respectively arranged in the first and second housing fingers A1;A2 of the housing A that are kept apart from each other within a short distance. In consequence, the sensing ranges of the first optical element A3 and the second optical element A4 is limited, lowering the turbidity sensing accuracy.
(2) Because the first and second housing fingers A1;A2 of the housing A have different lengths, it is difficult to keep the first optical element A3 and the second optical element A4 in accurate alignment. If the first optical element A3 and the second optical element A4 are not accurately aligned, the sensing accuracy will be affected.
(3) Suspended particles tend to be accumulated in the flow-retarding area around the outer side of the first optical element A3 in the first housing finger A1 and the outer side of the second optical element A4 in the second housing finger A2, affecting the sensing accuracy.
(4) The flowing direction and speed of the washing water will be changed due to performance of the sensing operation. Therefore, the washing water must be stopped when sensing the turbidity. However, suspended particles and impurities may float in the washing water when the washing water is stopped from flowing. The single-spot sensing method of the prior art design is not highly reliable. FIGS. 11 and 12 illustrate a flow velocity data obtained from the aforesaid prior art design through a computational fluid dynamics simulation.

Therefore, it is desirable to provide a turbidity sensor for use in a household appliance for sensing the turbidity of a fluid in a working chamber in the household appliance, which does not interfere with the flowing of the fluid in the working chamber and assures high sensing reliability and accuracy.

SUMMARY OF THE INVENTION

The present invention has been accomplished under the circumstances in view. It is the main object of the present invention to provide a turbidity sensor, which is practical for use in a household appliance for sensing the turbidity of a fluid in a working chamber in the household appliance without interfering with the flowing of the fluid in the working chamber, assuring high sensing reliability and accuracy.

To achieve this and other objects of the invention, a turbidity sensor is provided for installation in a household appliance for sensing the turbidity of a fluid in a working chamber in the household appliance, comprising a light-transmissive housing and a sensor module. The light-transmissive housing comprises a body shell, an accommodation chamber defined in the body shell and a hollow shank perpendicularly extending from the body shell and surrounding one side of the accommodation chamber and a cover member covering the accommodation chamber. The sensor module is mounted inside the light-transmissive housing for detecting the turbidity of the fluid in the working chamber of the household appliance, comprising a circuit board mounted in the accommodation chamber inside the body shell, a holder block supported on the circuit board, a set of light-transmitting devices mounted in the holder block and electrically connected to the circuit board and adapted for emitting light through the body shell onto the fluid in the working chamber of the household appliance, a set of light-receiving devices mounted in the holder block inside the hollow shank of the body shell in a right angle relationship relative to the light-transmitting devices and electrically connected to the circuit board for picking up reflected light from suspended particles/impurities in the fluid and producing a respective sensing signal for determination of the turbidity of the fluid and a connection interface extended from one side of the circuit board out of the cover member and electrically coupled with the circuit board for transmitting the respective sensing signal to external circuit means for computing the turbidity.

Further, the circuit board can be configured to provide a controller (CPU, chip, single crystal or microprocessor) for computing the mean value of the sensing signals produced by the light-receiving devices and then transmitting the mean value to the control circuit of the household appliance for turbidity determination. Alternatively, the circuit board can be configured to provide a controller (CPU, chip, single crystal or microprocessor) for computing the mean value of the sensing signals produced by the light-receiving devices and the comparing the mean value with a predetermined reference value to determine the turbidity of the fluid in the working chamber.

Further, the body shell is a hollow shell shaped like a stepped cylinder; the hollow shank and the cover member are respectively configured as one of circular, rectangular, oval and polygonal shapes. Further, the cover member comprises an opening cut through opposing front and back sides thereof and disposed in communication with the accommodation chamber and a connection base frame outwardly protruded from the front side around the opening. Further, the connection interface extends from the circuit board and is inserted through the opening into the inside of the connection base frame of the cover member. Further, the connection base frame can be configured subject to the configuration of a male connector or female connector for the connection of a mating female connector or male connector.

Further, the connection interface and said circuit board are joined together to show a cross-shaped configuration. The circuit board comprises a plurality of mounting holes cut through opposing top and bottom walls thereof. The holder block is configured to fit the configuration of the circuit board, comprising a plurality of bottom mounting rods respectively press-fitted into the respective mounting holes of the circuit board. Further, circuit board comprises a transverse body portion, a plurality of first via holes symmetrically located on two distal ends of the transverse body portion, a longitudinal body portion perpendicularly extended from a middle part of the transverse body portion and a plurality of second via holes located on the longitudinal body portion remote from the transverse body portion. Further, the light-transmitting devices are arranged in the holder block corresponding to the transverse body portion of the circuit board and respectively electrically bonded to the first via holes. Further, the light-receiving devices are arranged in the holder block corresponding to the longitudinal body portion of the circuit board and respectively electrically bonded to the second via holes.

Further, the holder block is T-shaped configuration, comprising a transverse holder block portion, a longitudinal holder block portion perpendicularly extended from a middle part of the transverse holder block portion, a plurality of first accommodation holes symmetrically located on two distal ends of the transverse holder block portion for accommodating the light-transmitting devices, a plurality of second accommodation holes bilaterally disposed near a distal end thereof remote from the transverse holder block portion for accommodating the light-receiving devices, a plurality of retaining hooks respectively disposed at one side of each of the first accommodation holes for securing the respective light-transmitting devices in the respective first accommodation holes, and a plurality of side notches respectively disposed at one side of each of the second accommodation holes corresponding to the light-receiving face of the associated light-receiving device.

Further, the body shell comprises two racks bilaterally disposed in the accommodation chamber and extending to an entrance of the accommodation chamber for holding the sensor module in the accommodation chamber. Each rack comprises a locating groove and a bearing wall disposed at an outer side thereof. The circuit board of the sensor module is mounted in the locating grooves of the two racks. The holder block of the sensor module is fastened to the circuit board and supported on the bearing walls of the two racks.

DETAILED DESCRIPTION OF THE PREFERRED EMBODIMENT

Figure 1:
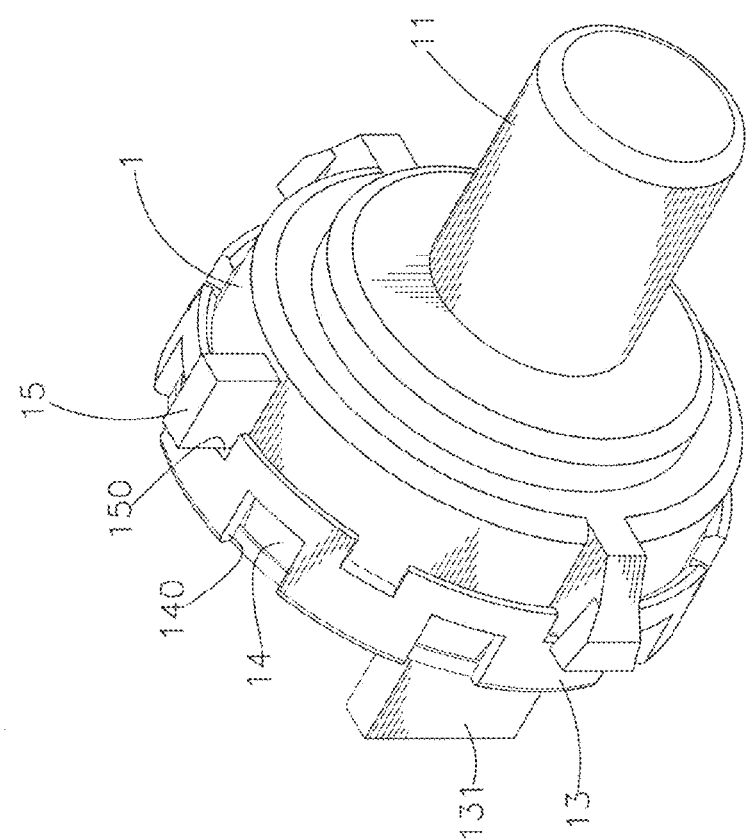
FIG. 1 is an elevational assembly view of a turbidity sensor in accordance with the present invention.
Figure 2:
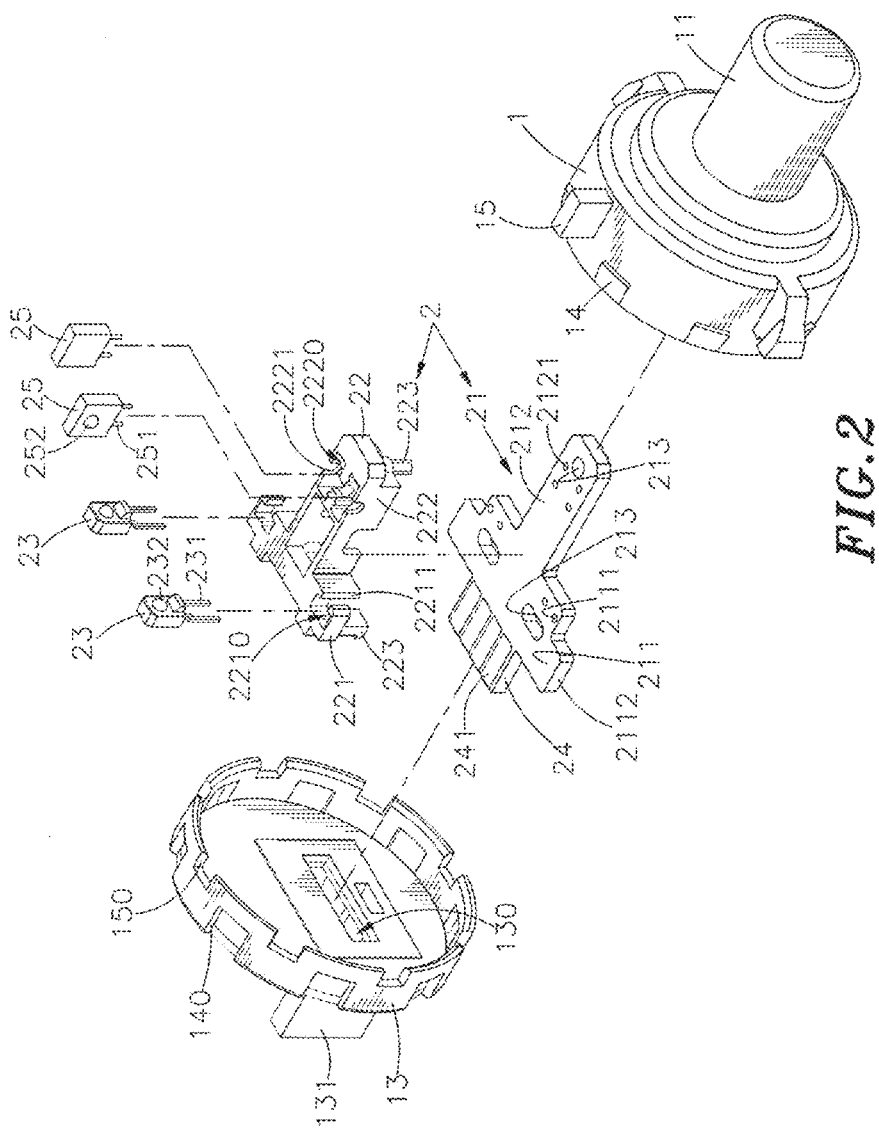
FIG. 2 is an exploded view of the turbidity sensor in accordance with the present invention.
Figure 3:
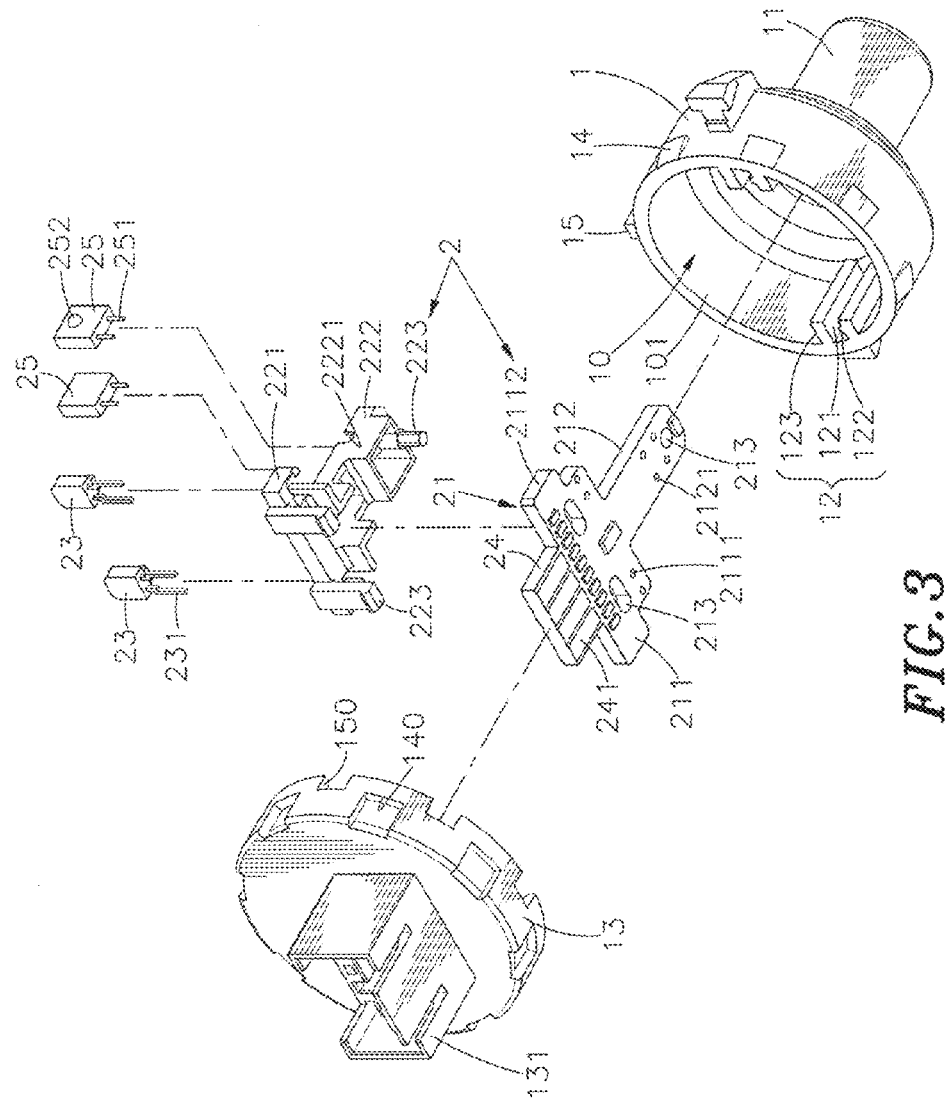
FIG. 3 is another exploded view of the turbidity sensor in accordance with the present invention when viewed from another angle.
Figure 4:
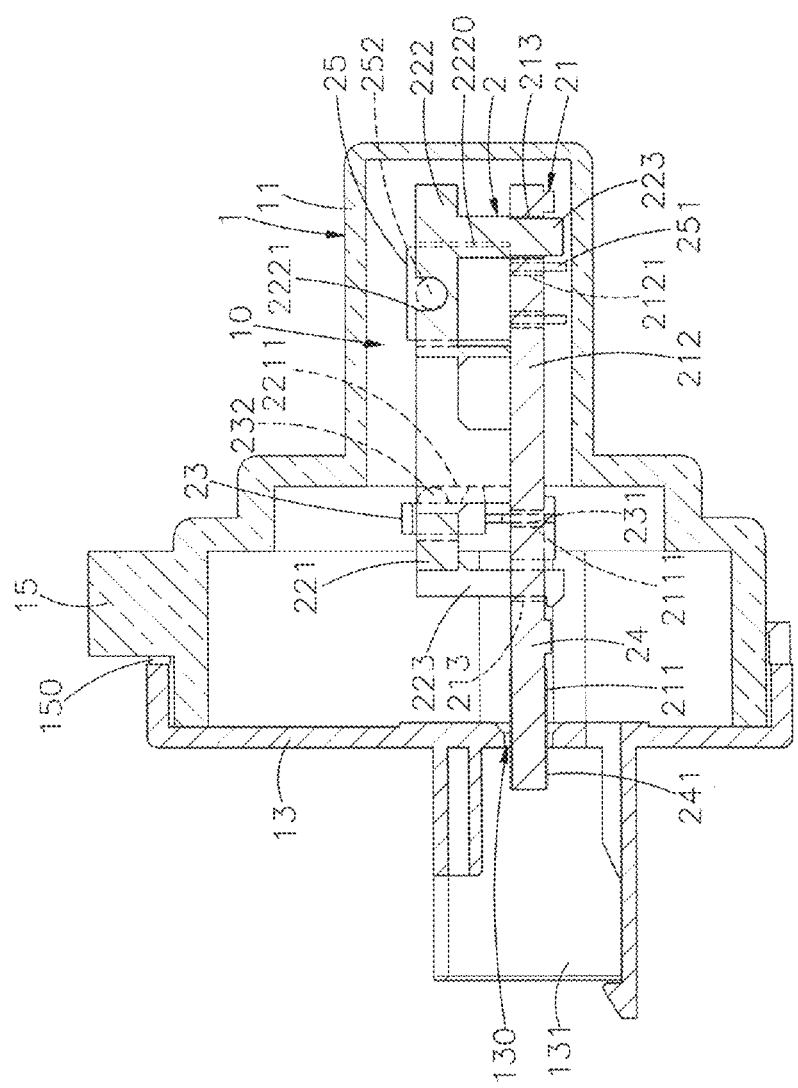
FIG. 4 is a sectional side view of the turbidity sensor in accordance with the present invention.

Referring to FIGS. 1~4, a turbidity sensor in accordance with the present invention is shown comprising a housing formed of a body shell 1 and a cover member 13, and a sensor module 20.

The body shell 1 and the cover member 13 are made of a light transmissive material. The body shell 1 is a hollow shell shaped like a stepped cylinder, comprising an accommodation chamber 10 having an entrance 101, a hollow shank 11 surrounding one side of the accommodation chamber 10 opposite to the entrance 101, and two racks 12 bilaterally disposed in the accommodation chamber 10. Each rack 12 comprises a locating groove 121, a locating flange 122 suspending in the locating groove 121 at one lateral side thereof, and a bearing wall 123 disposed at an outer side. The cover member 13 is capped on the body shell 1 to close the entrance 101 of the accommodation chamber 10, comprising an opening 130, which cuts through opposing front and back sides of the cover member 13 in communication with the entrance 101 of the accommodation chamber 10, and a connection base frame 131 outwardly protruded from the front side around the opening 130.

The sensor module 2 comprises a circuit board 21, a holder block 22, a plurality of light-transmitting devices 23, a connection interface 24 and a plurality of light-receiving devices 25. The circuit board 21 is T-shaped, comprising a transverse body portion 211 and a longitudinal body portion 212. The transverse body portion 211 comprises a plurality of via holes 2111 symmetrically located on two distal ends thereof and two locating wings 2112 respectively extended from the two distal ends. The longitudinal body portion 212 comprises a plurality of via holes 2121 arranged near a distal end thereof remote from the transverse body portion 211. The holder block 22 is configured to fit the T-shaped configuration of the circuit board 21 and mounted on the top side of the circuit board 21, comprising a transverse holder block portion 221 and a longitudinal holder block portion 222. The transverse holder block portion 221 comprises a plurality of first accommodation holes 2210 symmetrically disposed near two distal ends thereof and a retaining hook 2211 respectively disposed at one side of each of said first accommodation holes 2210. The longitudinal holder block portion 222 comprises a plurality of second accommodation holes 2220 bilaterally disposed near a distal end thereof remote from the transverse holder block portion 221 and a side notch 2221 respectively disposed at one side of each of said second accommodation holes 2220. The light-transmitting devices 23 are respectively mounted in said first accommodation holes 2210 of the transverse holder block portion 221 of the holder block 22 and secured thereto by the respective retaining hooks 2211, each comprising a plurality of electrode pins 231 respectively electrically bonded to the via holes 2111 of the transverse body portion 211 and a light-emitting face 232 exposed to the outside of a groove 2212 of the respective said first accommodation hole 2210 and facing the longitudinal direction corresponding to the extending direction of the longitudinal body portion 212. The connection interface 24 is formed integral with one side of the middle part of the transverse body portion 211 of the circuit board 21 opposite to the longitudinal body portion 212. Thus, the connection interface 24 and the circuit board 21 show a cross-shaped configuration. Further, the connection interface 24 comprises a plurality of metal contacts 241. The light-receiving devices 25 are respectively mounted in said second accommodation holes 2220 of the longitudinal holder block portion 222 of the holder block 22, each comprising a plurality of electrode pins 251 respectively electrically bonded to the via holes 2121 of the longitudinal body portion 212 and a light-receiving face 252 abutted to the respective side notch 2221 and facing toward the outside of the holder block 22 in the transverse direction corresponding to the extending direction of the transverse body portion 211.

Figure 5:
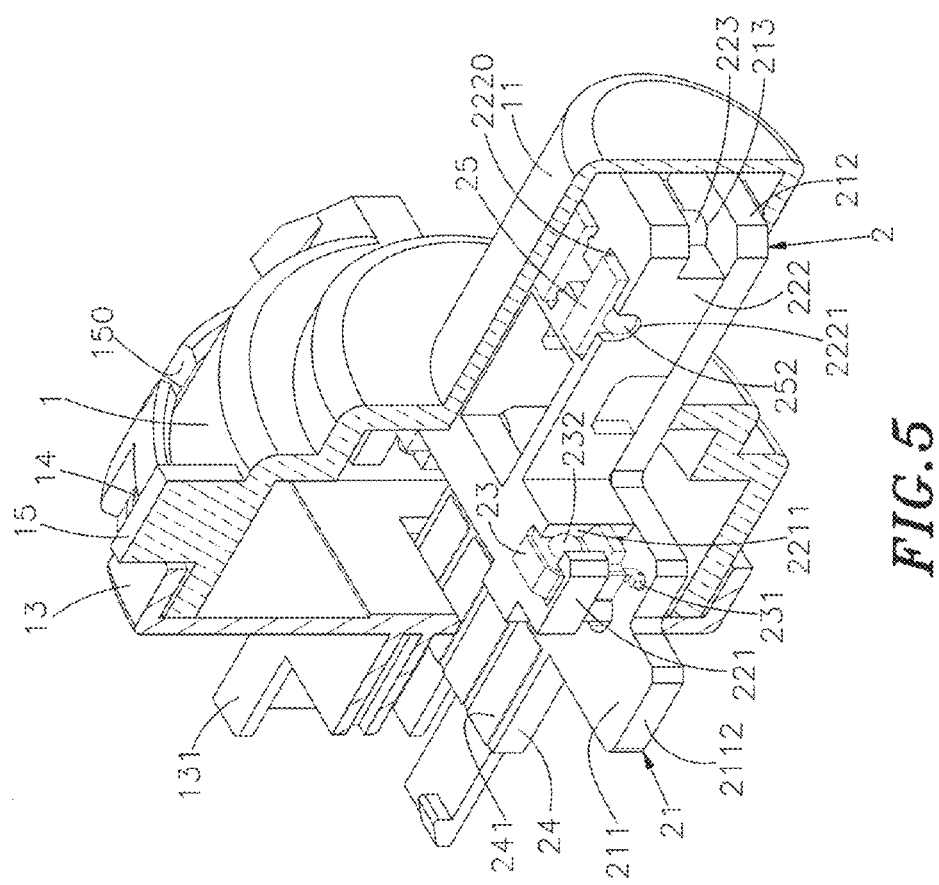
FIG. 5 is a sectional elevational view of the turbidity sensor in accordance with the present invention.
Figure 6:
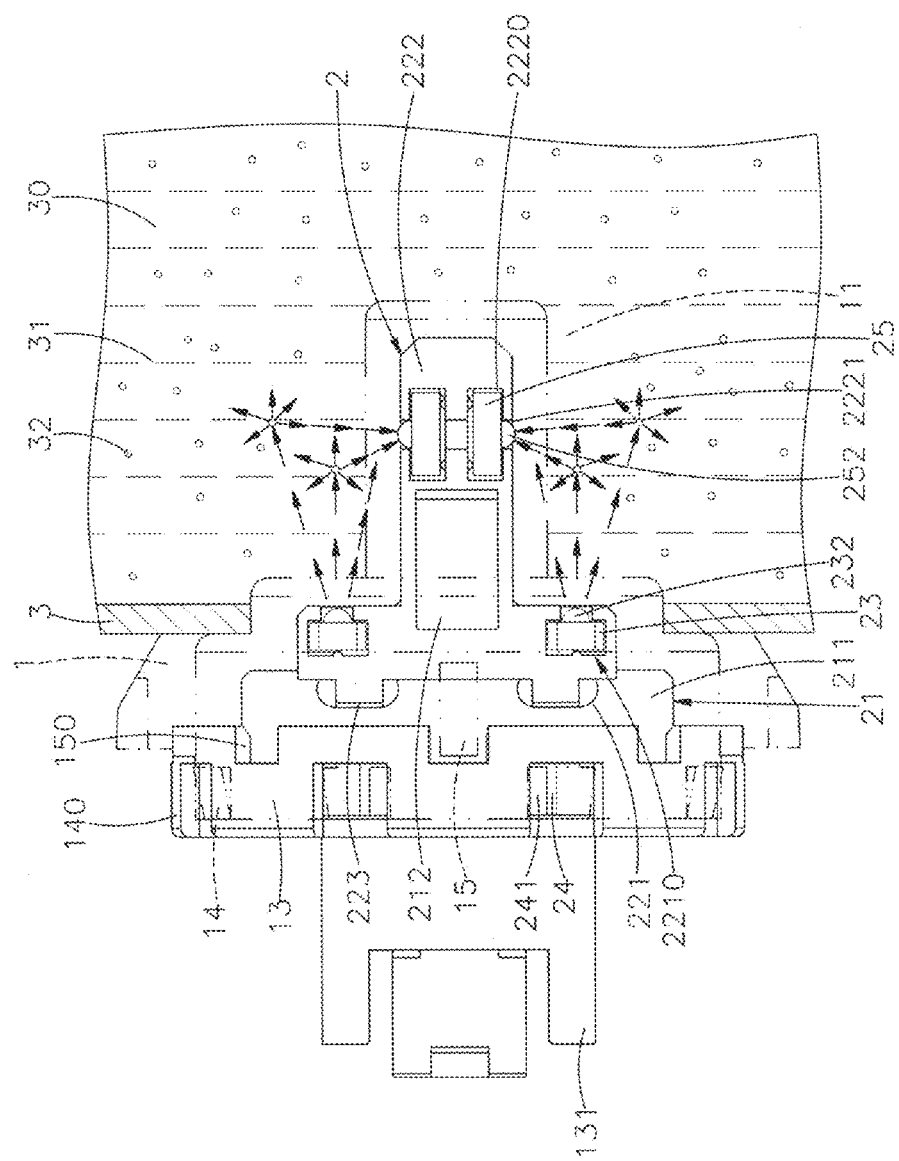
FIG. 6 is a schematic side view illustrating the turbidity sensor installed in a household appliance in accordance with the present invention.
Figure 7:
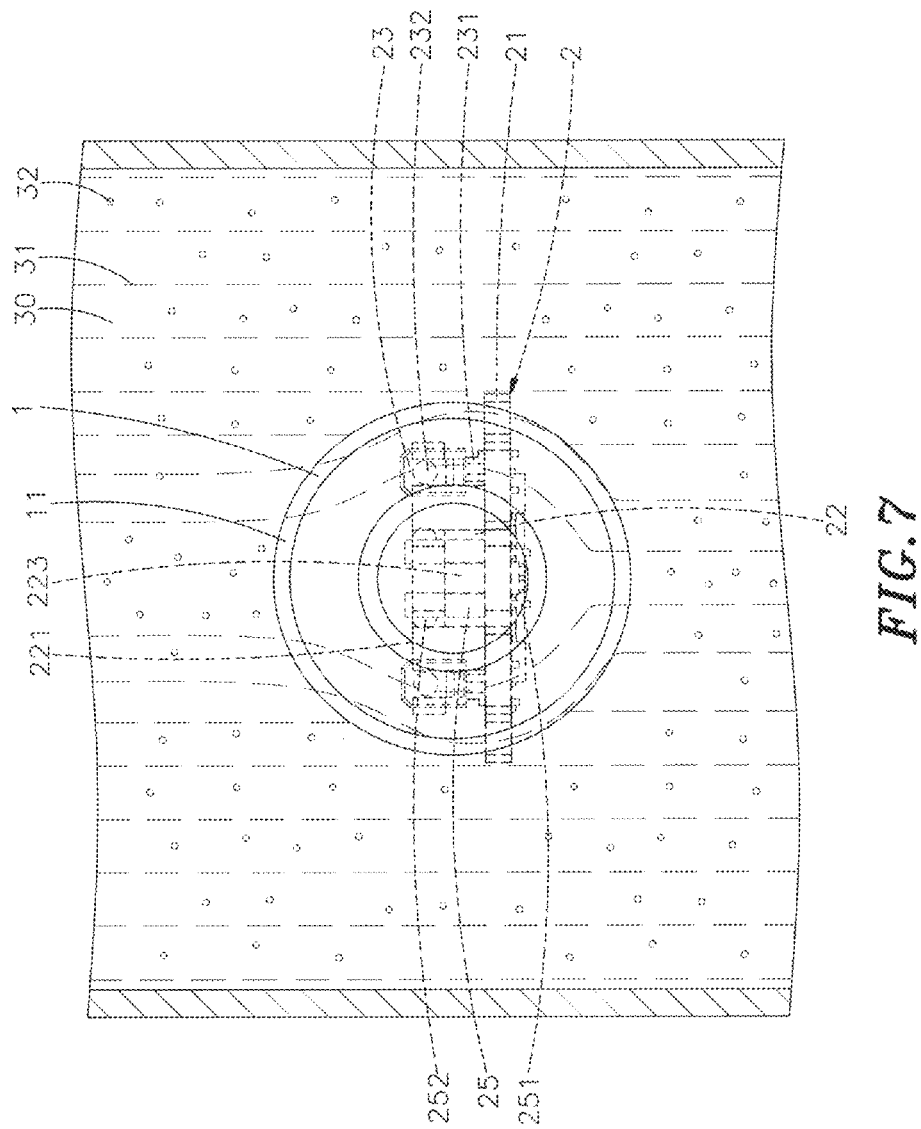
FIG. 7 is a top view of FIG. 6.

When assembling the turbidity sensor, insert the circuit board 21 with the holder block 22 through the entrance 101 into the accommodation chamber 10 of the body shell 1 to engage the two locating wings 2112 of the transverse body portion 211 of the circuit board 21 into the locating grooves 121 of the racks 12 respectively and to let the respective locating wings 2112 be secured to the respective racks 12 by the respective locating flanges 122. At this time, the holder block 22 is supported on the bearing walls 123 of the racks 12 respectively, the longitudinal body portion 212 of the circuit board 21; the longitudinal holder block portion 222 of the holder block 22 are positioned inside the hollow shank 11 of the body shell 1; the light-transmitting devices 23 and the light-receiving devices 25 are respectively held in the holder block 22 within the hollow shank 11 of the body shell 1 at a right angle relationship (see FIG. 4 and FIG. 5). Thereafter, cover the cover member 13 on the body shell 1 to let the connection interface 24 of the sensor module 2 extend through the opening 130 to the inside of the cover member 13 of the connection base frame 131. Thus, the turbidity sensor is assembled.

The body shell 1 further comprises a plurality of beveled retaining blocks 14 and a plurality of locating blocks 15 protruded from the periphery. The cover member 13 further comprises a plurality of retaining holes 140 and a plurality of locating notches 150 respectively forced into engagement with the beveled retaining blocks 14 and locating blocks 15 of the body shell 1. Alternatively, the retaining holes 140 and the locating notches 150 can be formed on the body shell 1, and the beveled retaining blocks 14 and locating blocks 15 can be formed on the cover member 13 for engagement with the retaining holes 140 and the locating notches 150 respectively. Further, the connection base frame 131 of the cover member 13 can be configured subject to the specification of a male connector (or female connector) for connection to a mating female connector (or male connector).

Further, as stated above, the body shell 1 and the cover member 13 are made of a light transmissive material. Further, the body shell 1 can be made having a circular, rectangular, oval or polygonal profile. Further, the hollow shank 11 of the body shell 1 can be made having a circular, rectangular, oval or polygonal profile.

Further, the circuit board 21 comprises a plurality of mounting holes 213; the holder block 22 comprises a plurality of bottom mounting rods 223 respectively press-fitted into the respective mounting holes 213 of the circuit board 21. Further, the light-transmitting devices 23 can be infrared light-emitting diodes, ultraviolet light-emitting diodes or laser light-emitting diodes. Further, the light-receiving devices 25 can be photo transistors, optical receivers or light sensors arranged at right angles relative to the respective light-transmitting devices 23 and adapted for receiving a part of the light emitted by the light-transmitting devices 23 and the light reflected by surrounding substances.

Figure 8:
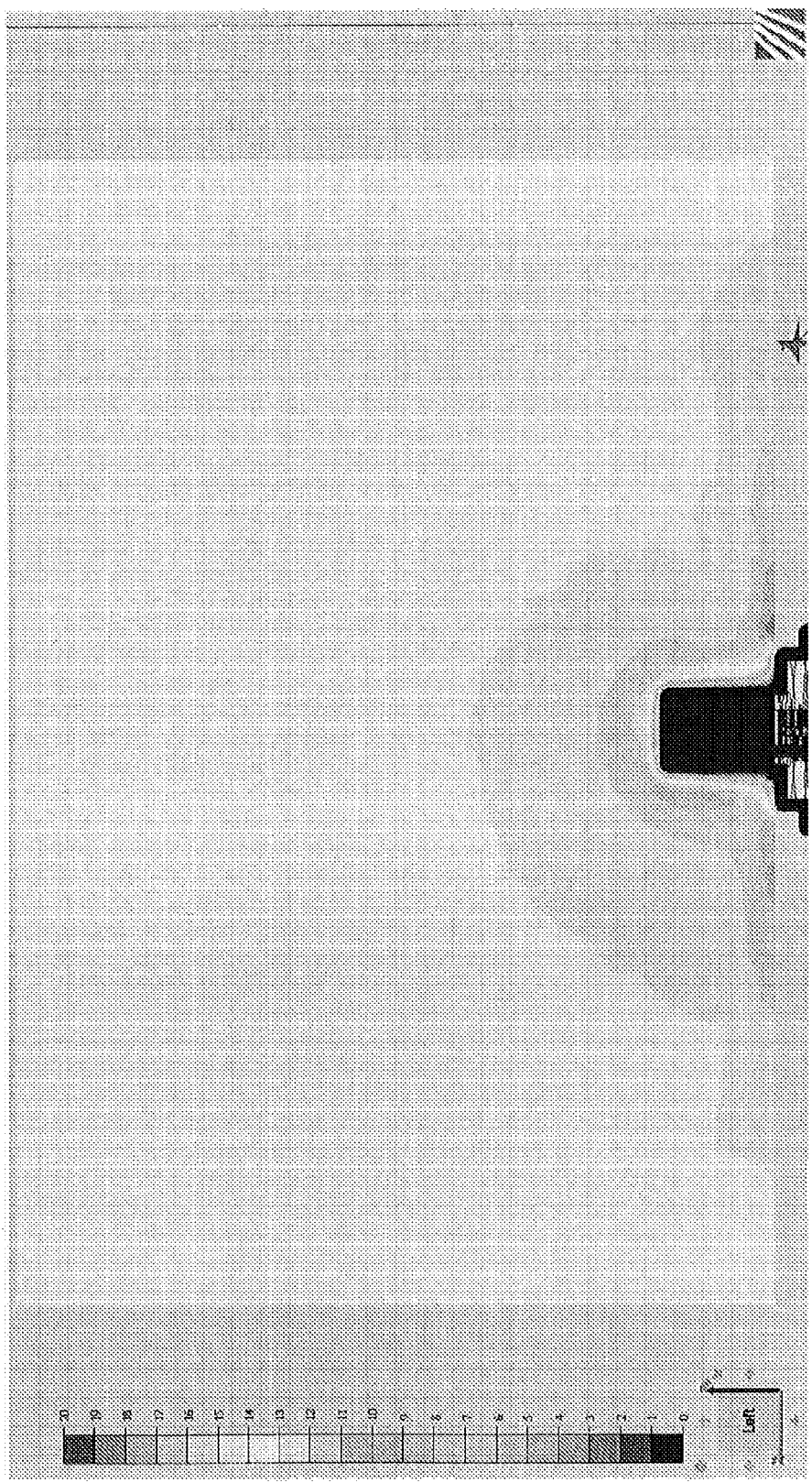
FIG. 8 is a schematic applied view of the present invention, illustrating a sensing operation of the turbidity sensor during flowing of a fluid therethrough (I).
Figure 9:
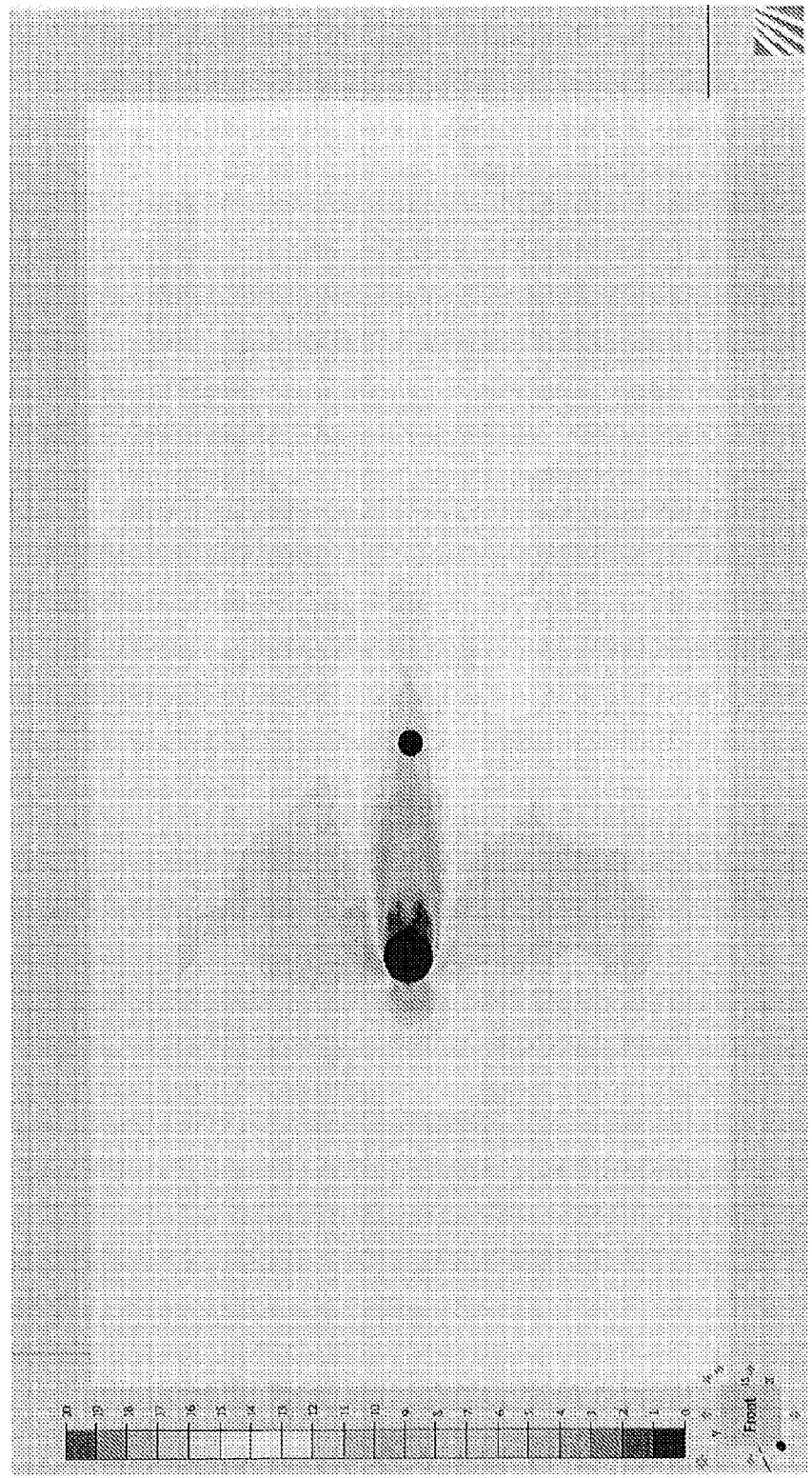
FIG. 9 is a schematic applied view of the present invention, illustrating a sensing operation of the turbidity sensor during flowing of a fluid therethrough (II).
Figure 10:
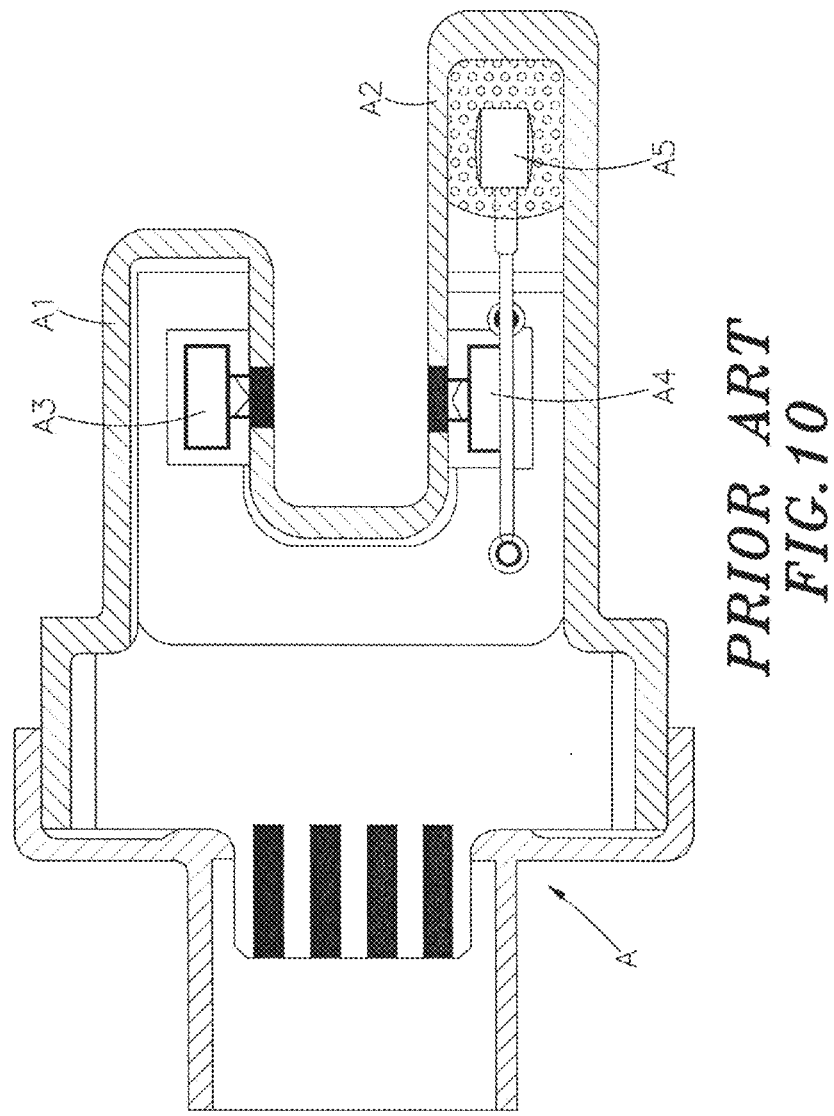
FIG. 10 is a sectional side view of a turbidity/temperature sensor according to the prior art.
Figure 11:
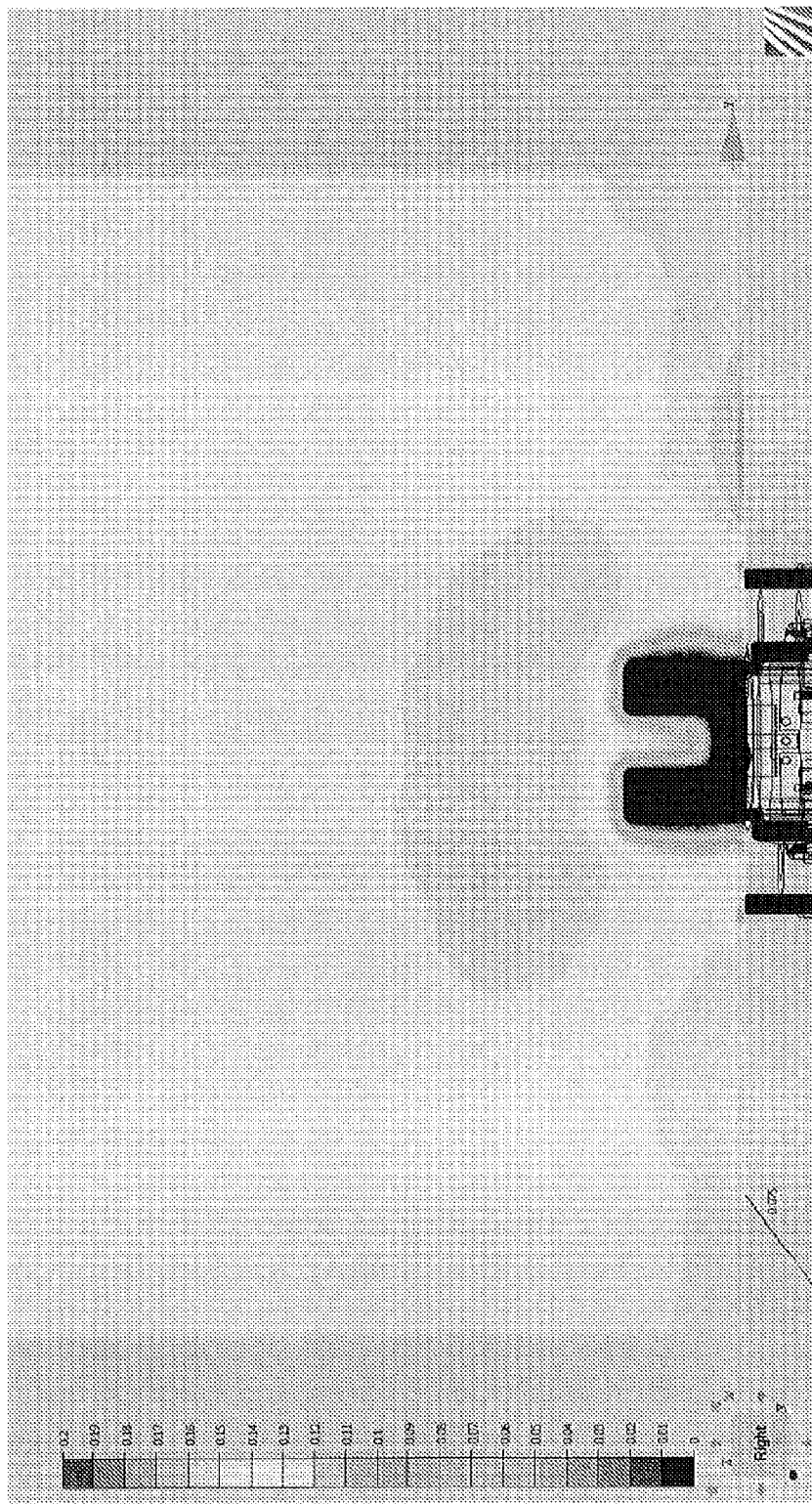
FIG. 11 is a schematic applied view of the prior art design, illustrating a sensing operation of the turbidity/temperature sensor during flowing of a fluid therethrough (I).
Figure 12:
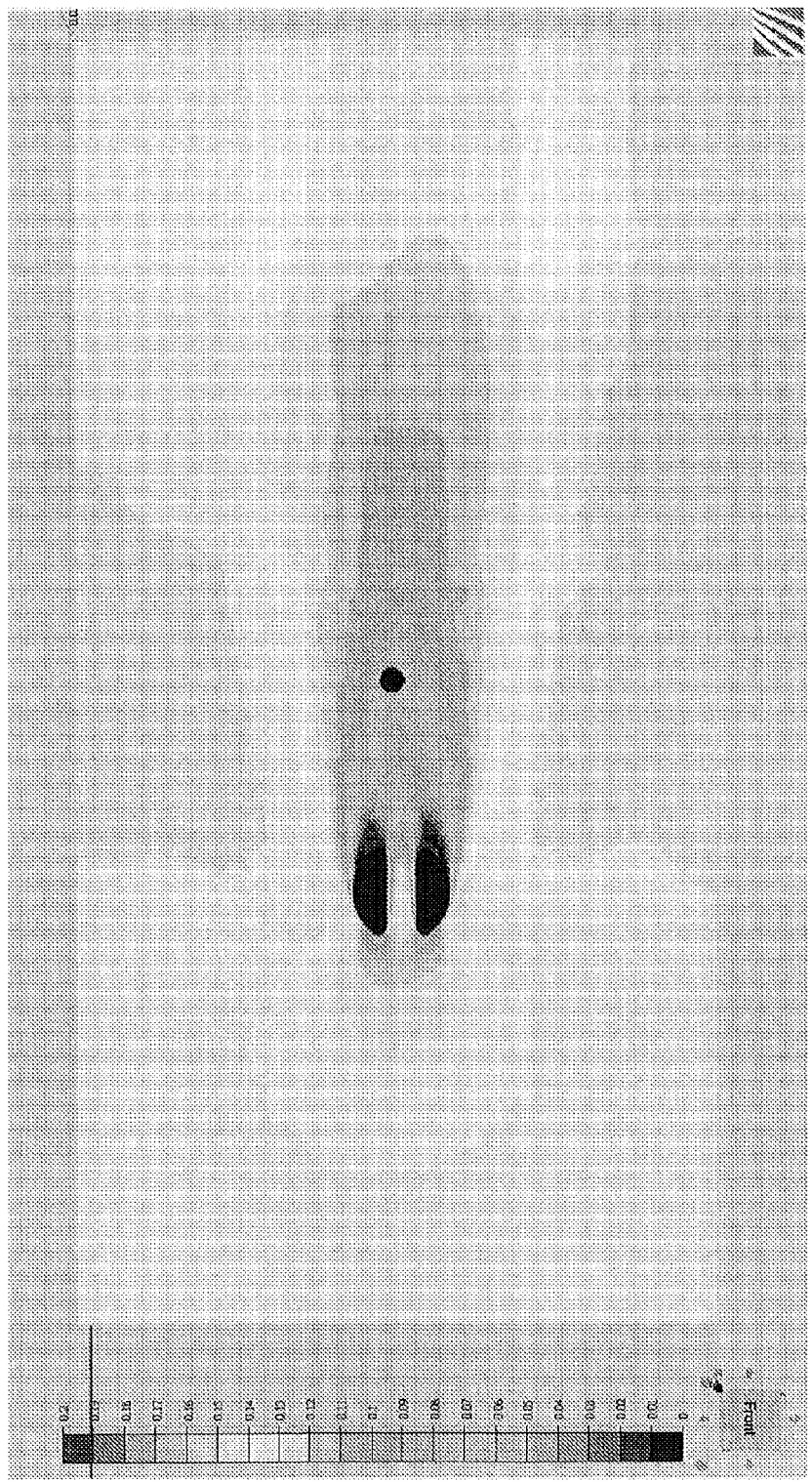
FIG. 12 is a schematic applied view of the prior art design, illustrating a sensing operation of the turbidity/temperature sensor during flowing of a fluid therethrough (II).

Referring to FIGS. 5~9 and FIGS. 2 and 4 again, when using the turbidity sensor in a household appliance 3, in particular washing machine or dishwasher, insert the hollow shank 11 of the body shell 1 into an internal working chamber 30 of the household appliance 3. When a fluid 31 is cycling in the working chamber 30, the hollow shank 11 of the body shell does not interfere with the flowing of the fluid 31 in the working chamber 30, avoiding accumulation of suspended particles or impurities 32. Thus, suspended particles or impurities 32 are evenly distributed in the fluid 31 during operation of the household appliance 3 (see the flow velocity data obtained using a computational fluid dynamics simulation as indicated in FIGS. 8 and 9), and the turbidity sensor can accurately detect the turbidity of the fluid 31 in the working chamber 30 without interrupting the operation of the household appliance 3. When the light-transmitting devices 23 emit light onto the fluid 31, the light-receiving devices 25 pick up reflected light from the evenly distributed suspended particles or impurities 32 in the fluid 31 for computing, assuring sensing accuracy. Therefore, the invention eliminates the inaccurate sensing problem of the prior art technique to sense the turbidity of a fluid that is kept still in a household appliance. Thus, when the turbidity sensor is used in a household appliance 3, it automatically starts sensing the turbidity of a fluid in the household appliance 3 during operation of the household appliance 3, i.e., it is not necessary to interrupt the operation of the household appliance 3 for allowing the turbidity sensor to sense the turbidity of the fluid in the household appliance 3.

During operation of the household appliance 3 to wash articles (clothes or dishes), a detergent may be added to the fluid 31 in the working chamber 30. Thus, the fluid 31 will become turbid due to the presence of the detergent and suspended particles or impurities 32 in the fluid 31. During working of the household appliance 3, the light-transmitting devices 23 of the sensor module 2 are controlled to emit light through the light-transmissive body shell 1 toward the inside of the working chamber 30. At this time, a part of the light emitted by the light-transmitting devices 23 of the sensor module 2 is received by the light-receiving devices 25. However, the major part of the light emitted by the light-transmitting devices 23 of the sensor module 2 falls upon the fluid 31 in the working chamber 30 into contact with suspended particles or impurities 32 in the fluid 31. Thus, the suspended particles or impurities 32 in the fluid 31 reflect the light, and the light-receiving devices 25 pick up reflected light from the suspended particles or impurities 32 and produce a respective sensing signal for transmission to a control circuit in the household appliance 3 by the circuit board 21 through the connection interface 24 in the connection base frame 131 of the cover member 13, so that the control circuit of the household appliance 3 can determine the turbidity of the fluid 31 in the working chamber 30 and control further operation steps subject to the turbidity of the fluid 31. As the method of the transmission of the sensing signals from the sensor module 2 to the control circuit of the household appliance 3 can easily be achieved by known techniques and is not within the scope of the spirit of the present invention, no further detailed description in this regard is necessary.

Except the aforesaid design to transmit sensing signals from the sensor module 2 to the control circuit of the household appliance 3 for turbidity determination, the circuit board 21 can be configured to provide a controller (CPU, chip, single crystal or microprocessor) for computing the mean value of the sensing signals produced by the light-receiving devices 25 and then transmitting the mean value to the control circuit of the household appliance 3 for turbidity determination. Alternatively, the circuit board 21 can be configured to provide a controller (CPU, chip, single crystal or microprocessor) for computing the mean value of the sensing signals produced by the light-receiving devices 25 and the comparing the mean value with a predetermined reference value to determine the turbidity of the fluid 31 in the working chamber 30.

As stated above, the invention provides a turbidity sensor for use in a household appliance 3 for sensing the turbidity of a fluid 31 in a working chamber 30 in the household appliance. The turbidity sensor comprises a body shell 1 that has an accommodation chamber 10 defined therein and a hollow shank 11 surrounding one side of the accommodation chamber 10, a cover member 13 covering the body shell 1, and a sensor module 2, which comprises a circuit board 21 mounted in the accommodation chamber 10 inside the body shell 1, a holder block 22 supported on the circuit board 21, a set of light-transmitting devices 23 mounted in the holder block 22 and electrically connected to the circuit board 21 for emitting light through the light-transmissive body shell 1 onto the fluid 31 in the working chamber 30 of the household appliance 3 and a set of light-receiving devices 25 mounted in the holder block 22 inside the hollow shank 11 of the body shell 1 in a right angle relationship relative to the light-transmitting devices 23 and electrically connected to the circuit board 21 for picking up reflected light from suspended particles or impurities 32 in the fluid 31 and producing a respective sensing signal for determination of the turbidity of the fluid 31. The turbidity sensor of the invention is adapted to detect the turbidity of the fluid 31 in the working chamber 30 of the household appliance 3 during operation of the household appliance 3 so that the control circuit of the household appliance 3 can control the operation of the household appliance 3 subject to the detection of the turbidity sensor without interrupting the operation of the household appliance 3.

In conclusion, the invention provides a turbidity sensor for use in a household appliance 3 for sensing the turbidity of a fluid 31 in a working chamber 30 in the household appliance 3, which has advantages as follows:

1. The light-transmitting devices 23 and the light-receiving devices 25 are arranged in a right angle relationship so that the light-transmitting devices 23 can emit light widely onto the fluid 31 in the working chamber 30 in the household appliance 3; the light-receiving devices 25 can pick up reflected light from evenly distributed suspended particles or impurities 32 in the fluid 31 to provide a respective sensing signal for accurate determination of the turbidity of the fluid 31.
2. The hollow shank 11 extends perpendicularly from the center of one side of the body shell 1 and suspending in the fluid 31 in the working chamber 30 inside the household appliance 3; the light-transmitting devices 23 are arranged on the transverse body portion 211 of the circuit board 21 in the light-transmissive body shell 1 beyond the hollow shank 11 to emit light through the light-transmissive body shell 1 onto the fluid 31 in the working chamber 30 in the household appliance 3; the light-receiving devices 25 are arranged on the longitudinal body portion 212 of the circuit board 21 inside the hollow shank 11 of the light-transmissive body shell 1 to effectively pick up reflected light from evenly distributed suspended particles or impurities 32 in the fluid 31. Thus, the sensor module 2 of the turbidity sensor can effectively and accurate detect the turbidity of the fluid 31 without adjustment.
3. After installation of the turbidity sensor in the household appliance 3, simply the hollow shank 11 of the light-transmissive body shell 1 is dipped in the fluid 31 in the working chamber 30 of the household appliance 3, and therefore the light-transmissive body shell 1 does not interfere with flowing of the fluid 31 in the working chamber 30 and, the turbidity sensor can effectively detect the turbidity of the fluid in the working chamber 30 without interrupting the operation of the household appliance 3.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A turbidity sensor for installation in a household appliance for sensing the turbidity of a fluid in a working chamber in said household appliance, the turbidity sensor comprising:
    a light-transmissive housing, said light-transmissive housing comprising a body shell, an accommodation chamber defined in said body shell and a hollow shank perpendicularly extending from said body shell and surrounding one side of said accommodation chamber and a cover member covering said accommodation chamber; and
    a sensor module mounted inside said light-transmissive housing for detecting the turbidity of said fluid in said working chamber of said household appliance, said sensor module comprising a circuit board mounted in said accommodation chamber inside said body shell, a holder block supported on said circuit board, a set of light-transmitting devices mounted in a first accommodation hole of said holder block and electrically connected to said circuit board and adapted for emitting light through said body shell onto said fluid in said working chamber of said household appliance, a set of light-receiving devices mounted in a second accommodation hole of said holder block inside said hollow shank of said body shell in a right angle relationship relative to said light-transmitting devices and electrically connected to the circuit board for picking up reflected light from suspended particles/impurities in said fluid and producing a respective sensing signal for determination of the turbidity of said fluid and a connection interface extended from one side of said circuit board out of said cover member and electrically coupled with said circuit board for transmitting said respective sensing signal to external circuit means;

wherein said connection interface and said circuit board are joined together to show a cross-shaped configuration; said circuit board comprises a plurality of mounting holes cut through opposing top and bottom walls thereof; said holder block is configured to fit the configuration of said circuit board, comprising a plurality of bottom mounting rods respectively press-fitted into the respective mounting holes of said circuit board; and wherein said circuit board comprises a transverse body portion, a plurality of first via holes symmetrically located on two distal ends of said transverse body portion, a longitudinal body portion perpendicularly extended from a middle part of said transverse body portion and a plurality of second via holes located on said longitudinal body portion remote from said transverse body portion; said light-transmitting devices are arranged in said holder block corresponding to said transverse body portion of said circuit board and respectively electrically bonded to said first via holes; said light-receiving devices are arranged in said holder block corresponding to said longitudinal body portion of said circuit board and respectively electrically bonded to said second via holes.

2. The turbidity sensor as claimed in claim 1, wherein said body shell is a hollow shell shaped like a stepped cylinder; said hollow shank and said cover member are respectively configured as one of circular, rectangular, oval and polygonal shapes.

3. The turbidity sensor as claimed in claim 1, wherein said cover member comprises an opening cut through opposing front and back sides thereof and disposed in communication with said accommodation chamber and a connection base frame outwardly protruded from the front side around said opening; said connection interface extends from said circuit board and is inserted through said opening into the inside of said connection base frame of said cover member.

4. The turbidity sensor as claimed in claim 1, wherein said body shell comprises two racks bilaterally disposed in said accommodation chamber and extending to an entrance of said accommodation chamber for holding said sensor module in said accommodation chamber.

5. The turbidity sensor as claimed in claim 4, wherein each said rack comprises a locating groove and a bearing wall disposed at an outer side thereof; said circuit board of said sensor module is mounted in the locating grooves of said two racks; said holder block of said sensor module is fastened to said circuit board and supported on the bearing walls of said two racks.

6. The turbidity sensor as claimed in claim 1, wherein each said light-transmitting device comprises a light-emitting face facing in a first direction corresponding to the extending direction of said longitudinal body portion of said circuit board; said light-receiving devices are symmetrically and reversely arranged in said holder block, each having a light-receiving face facing in a second direction perpendicular to said first direction and corresponding to the extending direction of said transverse body portion of said circuit board.

7. The turbidity sensor as claimed in claim 1, wherein said light-transmitting devices are selected from the group of infrared light-emitting diodes, ultraviolet light-emitting diodes and laser light-emitting diodes.

8. The turbidity sensor as claimed in claim 1, wherein said light-receiving devices are selected from the group of photo transistors, optical receivers and light sensors.

9. A turbidity sensor for installation in a household appliance for sensing the turbidity of a fluid in a working chamber in said household appliance, the turbidity sensor comprising:

a light-transmissive housing, said light-transmissive housing comprising a body shell, an accommodation chamber defined in said body shell and a hollow shank perpendicularly extending from said body shell and surrounding one side of said accommodation chamber and a cover member covering said accommodation chamber; and a sensor module mounted inside said light-transmissive housing for detecting the turbidity of said fluid in said working chamber of said household appliance, said sensor module comprising a circuit board mounted in said accommodation chamber inside said body shell, a holder block supported on said circuit board, a set of light-transmitting devices mounted in a first accommodation hole of said holder block and electrically connected to said circuit board and adapted for emitting light through said body shell onto said fluid in said working chamber of said household appliance, a set of light-receiving devices mounted in a second accommodation hole of said holder block inside said hollow shank of said body shell in a right angle relationship relative to said light-transmitting devices and electrically connected to the circuit board for picking up reflected light from suspended particles/impurities in said fluid and producing a respective sensing signal for determination of the turbidity of said fluid and a connection interface extended from one side of said circuit board out of said cover member and electrically coupled with said circuit board for transmitting said respective sensing signal to external circuit means;

wherein said connection interface and said circuit board are joined together to show a cross-shaped configuration; said circuit board comprises a plurality of mounting holes cut through opposing top and bottom walls thereof; said holder block is configured to fit the configuration of said circuit board, comprising a plurality of bottom mounting rods respectively press-fitted into the respective mounting holes of said circuit board; and wherein said holder block is T-shaped configuration, comprising a transverse holder block portion, a longitudinal holder block portion perpendicularly extended from a middle part of said transverse holder block portion, a plurality of first accommodation holes symmetrically located on two distal ends of said transverse holder block portion for accommodating said light-transmitting devices and a plurality of second accommodation holes bilaterally disposed near a distal end thereof remote from said transverse holder block portion for accommodating said light-receiving devices.

10. The turbidity sensor as claimed in claim 9, wherein said holder block further comprises a plurality of retaining hooks respectively disposed at one side of each of said first accommodation holes for securing said light-transmitting devices in said first accommodation holes, and a plurality of side notches respectively disposed at one side of each of said second accommodation holes corresponding to the light-receiving face of the associating light-receiving device.

* * * * *